United States Patent [19]

West et al.

[11] Patent Number: 5,386,048

[45] Date of Patent: Jan. 31, 1995

[54] HYDROSILYLATION OF FULLERENES

[75] Inventors: Robert C. West, Madison, Wis.; Kunio Oka, Osaka, Japan

[73] Assignee: Wisconsin Alumni Research Foundation, Madison, Wis.

[21] Appl. No.: 157,002

[22] PCT Filed: Feb. 26, 1993

[86] PCT No.: PCT/US93/01762

§ 371 Date: Nov. 24, 1993

§ 102(e) Date: Nov. 24, 1993

[87] PCT Pub. No.: WO94/19300

PCT Pub. Date: Sep. 1, 1994

[51] Int. Cl.$^6$ .............................. C07F 7/08; C07F 7/18
[52] U.S. Cl. ...................... 556/430; 556/432; 556/435; 556/452; 556/453; 556/457; 556/465; 556/479; 556/482; 556/489
[58] Field of Search .............. 556/430, 432, 435, 452, 556/453, 457, 465, 479, 482, 489

[56] References Cited

PUBLICATIONS

J. Speier, "Homogeneous Catalysis Hydrosilation by Transition Metals", 17 *Advances in Organometallic Chemistry* 407–477 (1979.

D. Parker, et al., High–Yield Synthesis, Separation, and Mass–Spectrometric Characterization of Fullerenes $C_{60}$ to $C_{266}$, 113 J. Am. Chem. Soc. 7499–7503 (1991).

A. Koch, et al., Preparation of Fullerenes with a Simple Benchtop Reactor, 56 J. Org. Chem. 4543–4545 (1991).

Curl, et al., Fullerenes, Scientific American 54–63 (Oct. 1991).

P. Bhyrappa et al., Improved Chromatographic Separation and Purification of $C_{60}$ and $C_{70}$ Fullerenes, J. Chem. Soc. Chem. Comm. 936–937 (1992).

Chemical Abstracts, Is it possible to recognize organic molecules by controlling silica gel surface?, 116:186757u (1992).

Bausch et al., Diamagnetic Polyanions of the $C_{60}$ and $C_{70}$ Fullerenes: Preparation, $^{13}C$ and $^7Li$ NMR Spectroscopic Observation, and Alkylation with Methyl Iodite to Polymethylated Fullerenes, 113 J. Am. Chem. Soc. 3205–3206 (1991).

S. Shi, et al., A Polyester and Polyurethane of Diphenyl $C_{61}$: Retention of Fulleroid Properties in a Polymer, 114 J. Am. Chem. Soc. 10656–10657 (1992).

E. Samulski, et al., Flagellenes: Nanophase–Separated, Polymer–Substituted Fullerenes, 4 Chem. Mater. 1153–1157 (1992).

H. Nagashima, et al., $C_{60}Pd_n$: The First Organometallic Polymer of Buckministerfullerene, J. Chem. Soc., Chem. Commun. 377–379 (1992).

D. Loy, et al., Synthesis of a $C_{60}$–p–Xylylene Copolymer, 114 Amer. Chem. Soc. 3977–3978 (1992).

I. Ojima, "The Hydrosilylation Reaction", *The Chemistry of Organic Silicon Compounds*, Edited by S. Patai, et al., 1479–1499 (1989).

*Primary Examiner*—Paul F. Shaver
*Attorney, Agent, or Firm*—Quarles & Brady

[57] ABSTRACT

The invention provides silicon substituted fullerene compounds. The compounds can form polymers or wrapped fullerenes. The compounds may be made by reacting an organo-silicon compound with a fullerene in the presence of a catalyst by a hydrosilylation reaction.

5 Claims, 7 Drawing Sheets

Prior Art

HYDROSILYLATION OF FULLERENES

BACKGROUND OF THE INVENTION

1. Technical Field

This invention relates generally to silicon-substituted fullerene compounds and methods of making them.

2. Background Art

Fullerenes are a recently discovered form of pure solid carbon. They are cage-like hollow structures comprised of hexagon and pentagon rings fused together to form ball shaped hollow molecules which resemble geodesic domes. Fullerenes may range from 32 carbons up to many hundreds of carbon atoms. A fullerene molecule containing 60 carbons ($C_{60}$) is the archetype, and is known as Buckminsterfullerene. For a general discussion of fullerenes, see R. Curl, et al., *Scientific American*, 54–63 (October 1991). The disclosure of this articles, and of all other articles referred to herein, are incorporated by reference as if fully set forth herein.

Fullerenes have been synthesized by decomposing graphite rods in the presence of helium. Graphite rod decomposition may be accomplished by electric arc, as discussed in A. Koch, et al., 56 *Journal of Organic Chemistry*, 4543–4545 (1991)($C_{60}$; $C_{70}$), or by plasma discharge as discussed in D. Parker; et al., 113 *Journal American Chemical Society*, 7499–7503 (1991)($C_{60}$–$C_{266}$).

Researchers have identified many interesting uses of fullerenes over the past few years. For example, fullerenes show promise for use in diamond films, nonlinear optical and superconducting materials, semiconductors, and photo-conductors. Because pure fullerenes form discreet crystals, more processable forms of fullerenes are needed to more fully exploit their unique properties.

A few polymers of fullerenes have been synthesized to help meet this need. In this regard, D. Loy, et al. synthesized a $C_{60}$-p-xylyene copolymer. See, 114 *Journal American Chemical Society*, 3977–3978 (1992). Another example is a palladium polymer of a Buckminsterfullerene synthesized by H. Nagashima, et al., *Journal of the Chemical Society*, "Chemical Communications", 377–379 (1992). Other examples are the synthesis by S. Shi, et al. of a polyester and polyurethane of diphenyl $C_{61}$. (See, 114 *Journal American Chemical Society*, 10656–10657 (1992)) and a polymer-substituted fullerene shown in E. Samulski, et al., 4 *Chemical Materials*, 1153–1157 (1992).

A drawback of some of the foregoing substituted fullerenes is that they employ expensive reagents, like palladium and xylylene. Further, some are made from reagents which have toxic side effects. Accordingly, there is a need for an inexpensive and non-toxic polymeric substituted fullerene.

Disclosure Of Invention

One aspect of the invention provides a compound having the moiety $C_n$—A—$C_m$ where $C_n$ and $C_m$ are ball-shaped, n and m are numbers above 59 and below 267, and A is a linker in which Si on the linker is directly attached to both $C_n$ and $C_m$. The linker preferably contains the moiety:

where $R_1$ through $R_4$ are selected from the group consisting of hydrogen, halide, aryl, alkyl, silyl, siloxy, and alkoxy, and where B is selected from the group consisting of nothing, oxygen, alkyl and aryl. Preferably, the alkyl and alkoxy groups contain from one to six carbons. The aryl preferably contains a phenyl moiety. This version of the invention is the polymeric version.

The preferred method for making these compounds is to conduct a hydrosilylation reaction between $C_n$, $C_m$, and at least two linker segments, wherein both linker segments have an SiH terminus.

Another version of the invention provides a compound having the moiety:

wherein $C_n$ is ball-shaped, n is a number above 59 and below 267, D is linked via Si bridges to at least two points on the $C_n$, and D contains a moiety that is selected from the group consisting of silane, siloxane, polysilane, and polysiloxane. In this aspect of the invention, a fullerene is "shrink-wrapped" by functional silicon moieties to form a somewhat rubbery substance.

The preferred method for making these compounds is to conduct a hydrosilylation reaction between $C_n$ and at least two linker segments, wherein both linker segments have an SiH terminus.

The invention therefore provides both polymers of fullerenes and wrapped fullerenes. These compounds have interesting properties for purposes of inter alia photoconducting. In both versions of the invention, $C_n$ preferably contains 60 or 70 carbon atoms.

The objects of the invention therefore include:
 (a) producing fullerenes of the above kind;
 (b) doing so using methods of the above kind; and
 (c) creating polymeric fullerenes that are relatively inexpensive and non-toxic.

These and still other objects and advantages of the present invention will be apparent from the description below.

BEST MODE FOR CARRYING OUT THE INVENTION

Figure 1:
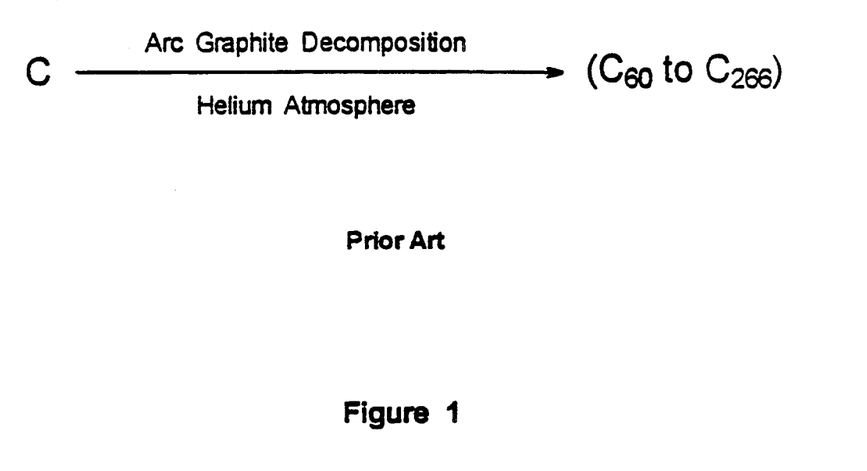
FIG. 1 is a schematic of the Example 1 prior art method of making unsubstituted fullerenes.

Example 1—Synthesis $C_{60}$ $C_{60}$ was synthesized using a benchtop graphite-vaporization apparatus according to Koch, et al., supra, and purified by continuous column chromatography according to P. Bhyrappa, et al., *J. Chem. Soc.*, 936–937 (1992). Purity was determined by size-exclusion chromatographic analysis. All glassware was flame-dried and allowed to cool under vacuum. Benzene was washed with concentrated $H_2SO_4$ until no darkening was observed and was then distilled from $CaH_2$ under dry argon.

Figure 2:
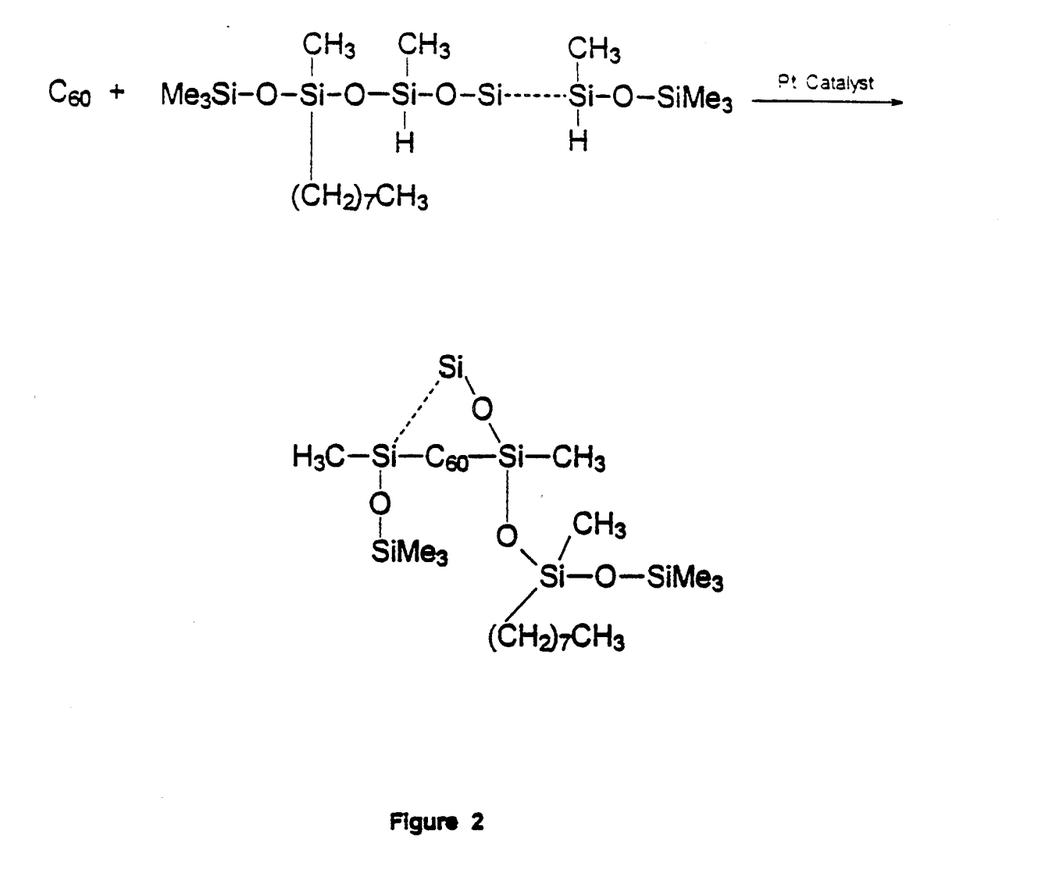
FIG. 2 is a schematic of the Example 2 synthesis.

Example 2-Platinum Catalyzed Hydrosilylation of $C_{60}$—"Shrink-Wrap"

Substrates (1) Buckminsterfullerene (>99.5% $C_{60}$)
(2) methylhydro (25-30%) methyloctyl (70-75%) siloxane copolymer; MW=5000-5500 dal.; DP≈36; Si-H equ./molecule=8−11

A 50 ml Schlenk flask was fitted with a septum and equipped with a teflon-coated magnetic stirring-bar. The flask was then purged with argon and 25 ml of benzene and 0.05 equ. of divinyltetramethyldisiloxane platinum (0) complex (the "catalyst") was added via a syringe. 210 mg (≈9equ.) of the siloxane copolymer was prediluted with 4 ml of benzene and was then introduced into the system. The Pt/siloxane mixture was allowed to stir for 15 mins. During this time it gradually changed from a colorless to dark-yellow solution.

30 mg of $C_{60}$ was then added under positive pressure and the mixture deoxygenated by argon displacement for ≈15 mins. The septum on the flask was replaced with a teflon stopper and the reaction mixture was stirred for 2 hrs. at 24° C. GPC analysis of the reaction mixture indicated full conversion of the fullerene to one product with little MW dispersion. The reaction mixture was then filtered through a short silica gel column to remove the platinum catalyst. The silica gel must be activated by heating at >110° C. for at least 2 hours.

The bulk of the benzene was removed from the filtrate with a slow $N_2$ flow, yielding a shiny, black solid (147 mg, 62% yield). This solid was placed in a vacuum chamber for 24 hrs to remove any remaining solvent. Infrared analysis indicated the absence of Si-H bonds of the starting siloxane in the product. The UV spectra was indicative of a highly substituted fullerene derivative. The adduct's $^1H$-NMR resonances were also measured. The compound was soluble in benzene, toluene, carbon disulfide; slightly soluble in tetrahydrofuran; and insoluble in common alcohols.

Figure 3:
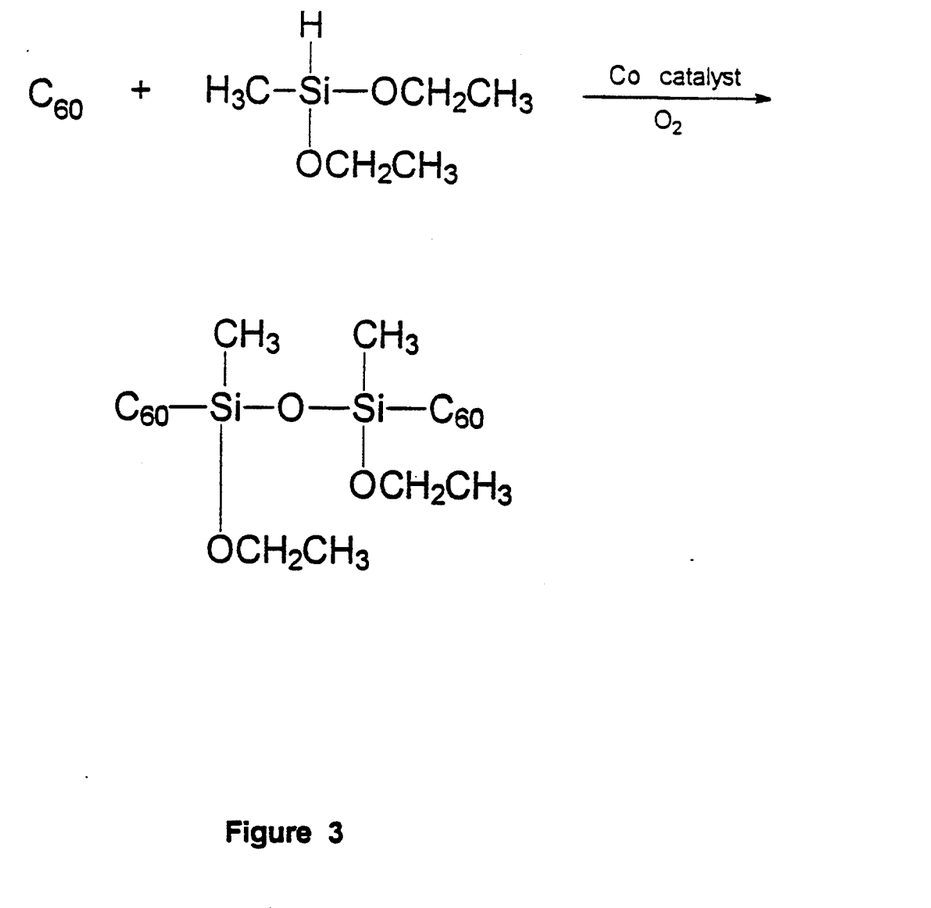
FIG. 3 is a schematic of the Example 3 synthesis.

Example 3—Hydrosilylation of $C_{60}$ by Methylethoxysilanes

The hydrosilylation reaction of $C_{60}$ was investigated from methylethoxysilanes using cobalt or platinum catalysts. Dimethylethoxysilane ($HSiMe_2(OEt)$), methyldiethoxysilane ($HSiMe(OEt)_2$), and triethoxysilane ($HSi(OEt)_3$) were used as a silane, while any one of dicobalt octacarbonyl ($CO_2(CO)_8$), chloroplatinic acid ($H_2PtCl_6 \cdot 8H_2O$), and platinum-silane complex ($PtL_2$, $L=H_2C=CHSiMeSiMe_2$—O—$SiMe_2CH=CH_2$) were used as a catalyst.

The reaction procedure of this hydrosilylation reaction was same for every combination of silane and catalyst. A representative procedure is described for the combination of methyldiethoxysilane and dicobalt octacarbonyl.

This reaction was carried out under argon atmosphere. $C_{60}$ (3.6 mg, 0.05 mmol) was dried under the vacuum for 0.5 h and then dissolved in 10 ml of benzene. Into a 50 ml of flask fitted with a conventional condenser, dicobalt octacarbonyl ($CO_2(CO)_8$, 1.6 mg, 0.005 mmol) and then methyldiethoxysilane ($HSiMe(OEt)_2$, 0.8 ml, 5 mmol) were placed with stirring for 0.5 h until the color of the solution turned to brown. Then the $C_{60}$-benzene solution was added to this solution. Stirring was continued at room temperature (about 25° C.) for four days with the addition of another portion of dicobalt octacarbonyl (0.6 mg, 0.005 mol) every 24 hrs. The total amount of the catalyst was 6.4 mg (0.2 mmol).

Solid material was filtered off and the benzene was evaporated under vacuum, followed by addition of diethyl ether. Unreacted $C_{60}$ was filtered from this diethyl ether solution, and the product was obtained by the evaporation of diethyl ether. (Yield: 38.2 mg)

Figure 4:
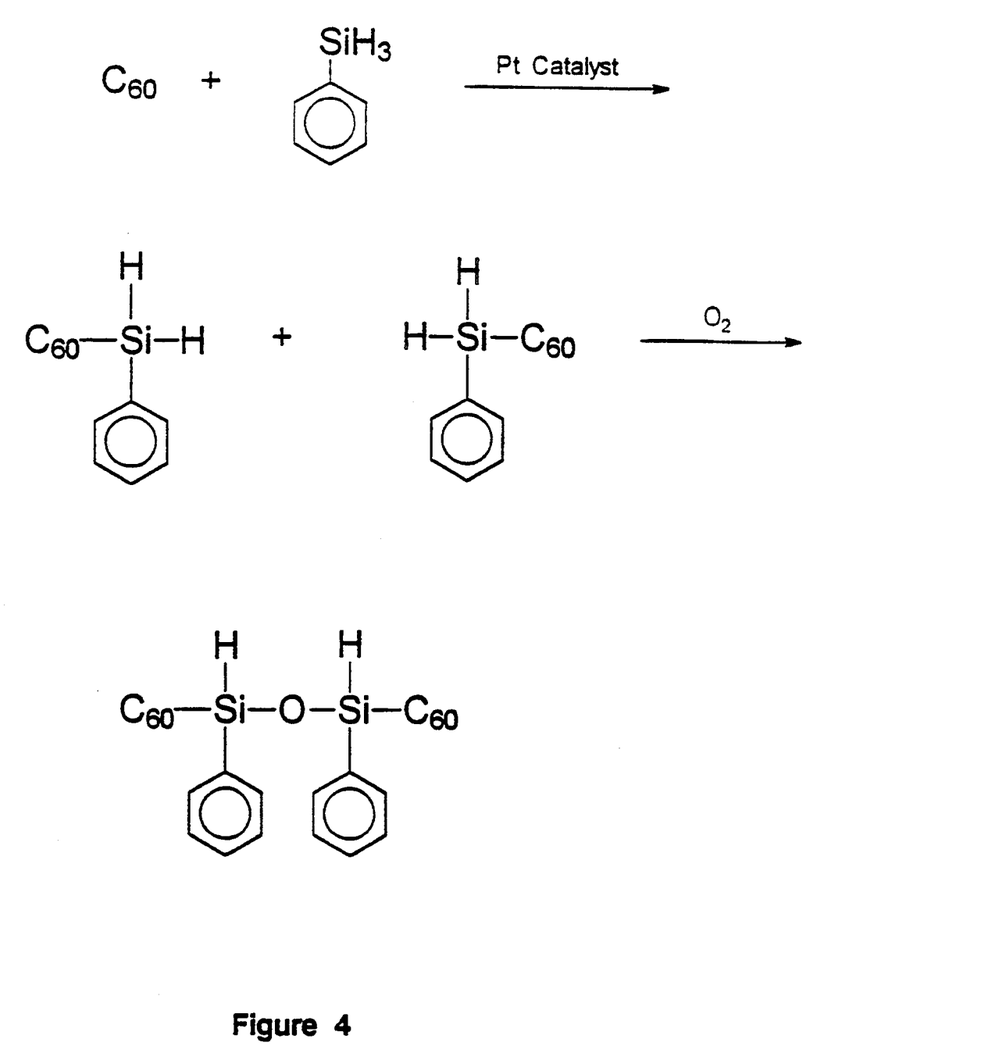
FIG. 4 is a schematic of the Example 4 synthesis.

Example 4—Reaction of $C_{60}$ With Phenylsilane

In a 100 mL flask was placed 33.3 mg of $C_{60}$, 1 mL of phenylsilane, 10 mL of benzene and 30.3 mg of chloroplantinic acid. The mixture was kept refluxing for three days under nitrogen. A black-brown solid was obtained after evaporation of the benzene. The product showed featureless UV absorption with tailing up to 500 nm. The product became insoluble solid after passing through aluminum oxide column, due to oxidation.

Similar reactions were carried out using diphenylsilane, hexylsilane, and dimethylchlorosilane. For example, in a 100 mL flask was placed 50 mg of $C_{60}$, 1 mL of phenyldimethylsilane, 10 mL of benzene and 19 mg of dicobalt octacarbonyl. A procedure similar to the above gave a black-brown solid.

Figure 5:
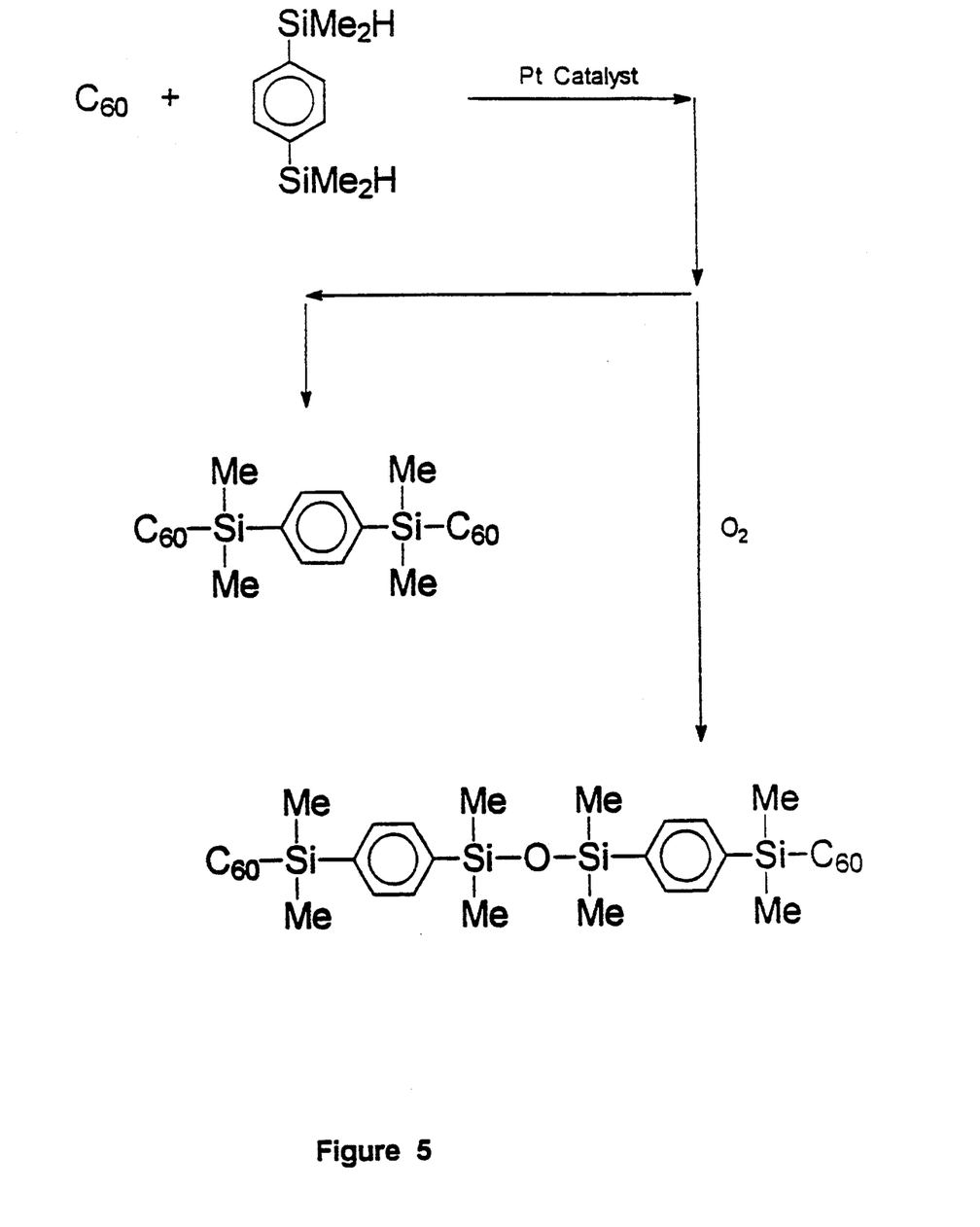
FIG. 5 is a schematic of the Example 5 synthesis.

Example 5—Reaction of $C_{60}$ with 1,4-bis(dimethylsilyl)benzene Catalyzed By Platinum bis(1,3-divinyltetramethyldisiloxane) Complex In a 100 mL flask 77 mg of $C_{60}$, 1 mL of 1,4-bis(dimethylsilyl)benzene, 50 mL of benzene and 25 μL of platinum bis(1,3-divinyltetramethyldisiloxane) complex at room temperature under an argon atmosphere. The mixture was kept at reflux for 1 day, during when time the characteristic purple color of $C_{60}$ disappeared. After an additional 25 μL of the complex was added and refluxing was continued for 1 day, this procedure was repeated two more times in order to consume all the $C_{60}$. After this time no $C_{60}$ was detected by GPC. Evaporation of benzene gave black-brown solid.

GPC analysis showed that there were two main peaks; one was at 13 mL and the other around 5–9.5 mL which composed from complex peaks. UV spectrum of the former fraction resembled to that of original $C_{60}$ and the latter fraction lost the characteristic feature of $C_{60}$ spectrum, suggesting that the product at 13 mL had smaller numbers of substituents and the product at 5–9.5 mL had multisubstituents.

Fractionation with ether and subsequently with benzene gave two fractions. The ether fraction contained mainly multi-substituted products and the benzene fraction contained $C_{60}$ and products with smaller number of substituents (determined by GPC).

Similar reactions were carried our using chloroplatinic acid or dicobalt octacabonyl as the catalyst and gave similar results.

Figure 6:
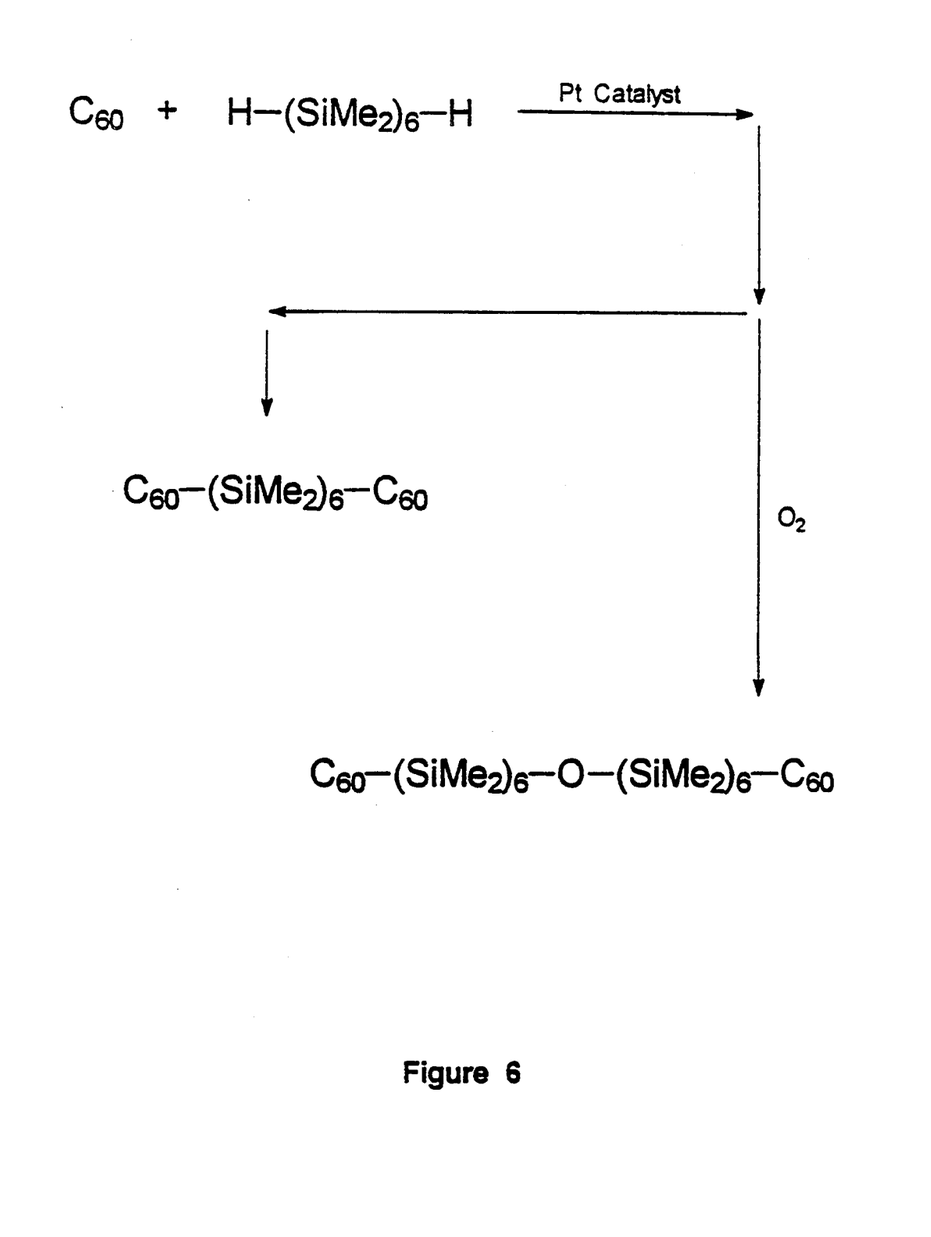
FIG. 6 is a schematic of the Example 6 synthesis.

Example 6—Reaction Of $C_{60}$ With 1,6-dihydrododecamethylhexasilane Catalyzed By Chloroplatinic Acid To a 50 mL of flask added 173 mg of $C_{60}$, 82.1 mg of $H(SiMe_2)_6H$, 100 mL of benzene, and 120 mg of chloroplatinic acid. The starting silane disappeared after refluxing the mixture for 3 days. Evaporation of the volatile material gave brown solid. Washing with hexane and subsequent elution with benzene from $Al_2O_3$ column in the presence of $O_2$ gave wine-red solution. A light brown solid was obtained after evaporation of benzene.

Successful hydrosilylation reactions with the same silane were also carried out using Pt/C and dicobalt octacarbonyl as catalysts.

Figure 7:
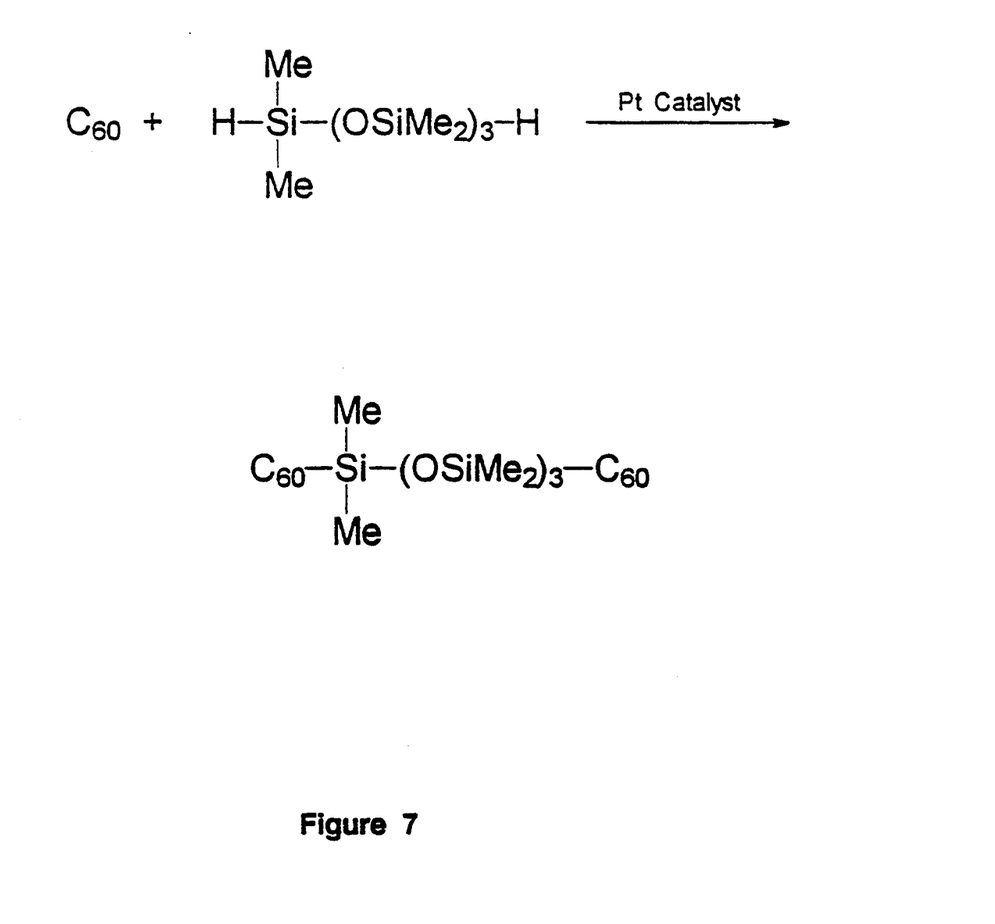
FIG. 7 is a schematic of the Example 7 synthesis.

Example 7—The Reaction Of $C_{60}$ and 1,1,3,3,5,5,7,7-Octamethyltetrasiloxane With Platinum Divinyltetramethyldisiloxane Complex Platinum divinyltetramethyldisiloxane complex (21 mg, 0.006 mmol) was added to a solution of $C_{60}$ (43 mg, 0.06 mol) and octamethyltetrasiloxane (179 mg, 0.6 mmol) in 6 ml of benzene at room temperature. The color of the reaction solution changed from purple to dark brown. The reaction mixture was refluxed for 4 h under nitrogen, but only small amounts of products besides $C_{60}$ was detected by GPC. Additional octamethyltetrasiloxane (179 mg, 0.6 mmol) and platinum divinyltetramethyldisiloxane complex (40 mg, 0.012 mmol) were added, and refluxing was continued. After 1 day, GPC showed an increased amount of products, but a large amount of $C_{60}$ still remained unreacted. More octamethyltetrasiloxane (720 mg, 2.4 mmol) and platinum divinyltetramethyldisiloxane complex (147 mg, 0.042 mmol) were added in total and the reaction mixture was allowed to reflux for 3 days. Only reaction products were detected by GPC.

After evaporation of the solvent, ether was added. The solution was filtered to remove any insoluble $C_{60}$ and the solvent evaporated. The remaining black semisolid, 849 mg, was soluble in organic solvent such as THF and chloroform, but became insoluble after some hours at room temperature in the absence of solvent. Yield: 848 mg.

Other Variants

Although the present invention has been described with reference to certain preferred embodiments, other versions are possible. For example, the "shrink-wrap" version may include a multiplicity of Si linkages and the fullerenes may include up to 266 carbons. Note also that the "moiety" language in the claims is intended to indicate that each $C_n$ or $C_m$ often also react with multiple SiH groups such that the final compound is a crosslinked grid with each fullerene ball linked to many other fullerene balls. Therefore, the scope of the claims should not be limited to the description of the preferred versions contained herein.

Industrial Applicability

These compounds have potential utility as photoconductors.

We claim:

1. A chemical compound having the following moiety:

where $C_n$ and $C_m$ are ball-shaped, n and m are numbers above 59 and below 267, and A is a linker in which Si on the linker is directly attached to both $C_n$ and $C_m$.

2. The compound of claim 1, wherein A contains the following moiety:

where $R_1$ through $R_4$ are selected from the group consisting of hydrogen, halide, aryl, alkyl, and alkoxy, and where B is selected from the group consisting of nothing, oxygen, alkyl and aryl.

3. A compound having the following moiety:

where $C_n$ is ball-shaped, n is a number above 59 and below 267, D contains a moiety selected from the group consisting of silane, siloxane, polysilane, and polysiloxane, and D is linked via Si bridges to at least two points on the $C_n$.

4. A method for making the compound of claim 1, comprising conducting a hydrosilylation reaction between $C_n$, $C_m$, and at least two linker segments, wherein both linker segments have an SiH terminus.

5. A method for making the compound of claim 3, comprising conducting a hydrosilylation reaction between $C_n$ and at least two linker segments, wherein both linker segments have an SiH terminus.

* * * * *